United States Patent
Moreau et al.

(10) Patent No.: US 10,365,246 B2
(45) Date of Patent: Jul. 30, 2019

(54) ULTRASOUND METHOD AND DEVICE FOR REPRESENTING THE PROPAGATION OF ULTRASOUND WAVES IN A GUIDE OF LINEARLY VARIABLE THICKNESS

(71) Applicants: Azalée, Paris (FR); Centre National de la Recherche Scientifique, Paris (FR); Université Pierre et Marie Curie—Paris 6, Paris (FR)

(72) Inventors: Ludovic Moreau, Paris (FR); Jean-Gabriel Minonzio, Paris (FR); Maryline Talmant, Vernon (FR); Pascal Laugier, Paris (FR)

(73) Assignees: Azalée, Paris (FR); Centre National de la Recherche Scientifique, Paris (FR); Université Pierre et Marie Curie - Paris 6, Paris (FR)

( * ) Notice: Subject to any disclaimer, the term of this patent is extended or adjusted under 35 U.S.C. 154(b) by 750 days.

(21) Appl. No.: 14/906,574

(22) PCT Filed: Jul. 4, 2014

(86) PCT No.: PCT/EP2014/064346
§ 371 (c)(1),
(2) Date: Jan. 21, 2016

(87) PCT Pub. No.: WO2015/010878
PCT Pub. Date: Jan. 29, 2015

(65) Prior Publication Data
US 2016/0161450 A1    Jun. 9, 2016

(30) Foreign Application Priority Data
Jul. 22, 2013 (FR) .................. 13 57204

(51) Int. Cl.
A61B 8/00 (2006.01)
A61B 8/08 (2006.01)
G01N 29/06 (2006.01)

(52) U.S. Cl.
CPC ......... G01N 29/069 (2013.01); A61B 8/0875 (2013.01); A61B 8/4494 (2013.01);
(Continued)

(58) Field of Classification Search
CPC ... A61B 8/0875; A61B 8/4494; A61B 8/5207; G01N 29/069; G01N 2291/02483; G01N 2291/106
See application file for complete search history.

(56) References Cited

U.S. PATENT DOCUMENTS

| | | | | |
|---|---|---|---|---|
| 6,468,215 | B1 * | 10/2002 | Sarvazyan | A61B 8/0875 600/438 |
| 2012/0111116 | A1 * | 5/2012 | Minonzio | A61B 8/0875 73/597 |

FOREIGN PATENT DOCUMENTS

| | | |
|---|---|---|
| FR | 2 946 753 A1 | 12/2010 |
| WO | 03/099133 A1 | 12/2003 |

OTHER PUBLICATIONS

Jean-Gabriel Minonzio et al.; Measurement of guided mode wave vectors by analysis of the transfer matrix obtained with multi-emitters and multi-receivers in contact; Conference date: Jan. 18, 2010-Jan. 22, 2010; Journal of Physics: Conference Series; vol. 269, No. 1; 6th Groupe De Recherche (GDR) 2501 and 9th Anglo-French Physical Acoustics Join.*
Machine translation of WO 03/099133 A1.*
Bruce W. Drinkwater et al.; Ultrasonic arrays for non-destructive evaluation: A review; NDT & E International; vol. 39, Issue 7, Oct. 2006, pp. 525-541.*

(Continued)

*Primary Examiner* — Amanda Lauritzen Moher
*Assistant Examiner* — Chao Sheng
(74) *Attorney, Agent, or Firm* — Osha Liang LLP

(57) ABSTRACT

Device for the representation, in a frequency-wave number reference frame f-k, of the propagation of an ultrasound (Continued)

wave in a dihedral guide (1), which comprises ultrasound emitters (2) referenced by "Ej" with j an integer varying between 1 and N, N a strictly positive integer and ultrasound receivers (3) referenced by "Ri" with i an integer varying between 1 and M, M a strictly positive integer, the receivers being disposed spatially over a first segment of a straight line according to a regular pitch "A", which comprises means for processing the signal received by the receivers, originating from the emitters, and in which the processing means comprise means for calculating a modified discrete spatial Fourier transform, for a spatial integration variable "x", centered in the middle of said first segment and running through the receivers in the direction of increasing x, and for a wave vector k(x) equal to a product k.P(x), with k a constant coefficient in x and included between 0 and 2*Pi/A, and with P(x) a polynomial in x, of coefficient of degree 0 in x equal to 1 and of coefficient "C" of degree 1 in x such that C.A lies between $-\frac{1}{10}$ and $+\frac{1}{10}$ 9 Claims, 2 Drawing Sheets

(52) U.S. Cl.
CPC .. *A61B 8/5207* (2013.01); *G01N 2291/02483* (2013.01); *G01N 2291/106* (2013.01)

(56) References Cited

OTHER PUBLICATIONS

J.U. Quistgaard; Signal acquisition and processing in medical diagnostic ultrasound; IEEE Signal Processing Magazine; vol. 14, Issue: 1, Jan 1997; pp. 67-74.*

Christensen, Ole et al.; Approximation Theory: From Taylor Polynomials to Wavelets; published in 2005 (2nd printing); publisher: Springer-Science+Business Media New York; p. 32.*

Josquin Foiret et al.; Cortical bone quality assessment using quantitative ultrasound on long bones; IEEE; 2012 Annual International Conference of the IEEE Engineering in Medicine and Biology Society; Date of Conference: Aug. 28-Sep. 1, 2012; pp. 1121-1124 (Year: 2012).*

International Search Report issued in corresponding application No. PCT/EP2014/064346 dated Oct. 21, 2014 (2 pages).

Written Opinion issued in corresponding application No. PCT/EP2014/064346 dated Oct. 21, 2014 (6 pages).

Josquin Foiret, et al.; "Guided mode measurement on bone phantoms with realistic geometry"; 2011 IEEE International Ultrasonics Symposium Proceedings, pp. 1610-1613; Oct. 18, 2011 (4 pages).

Jiangang Chen, et al.; "Measurement of guided mode wavenumbers in soft tissue-bone mimicking phantoms using ultrasonic axial transmission"; 2012 Institute of Physics and Engineering in Medicine, vol. 57, No. 10, pp. 3025-3037; Apr. 26, 2012 (13 pages).

* cited by examiner

ULTRASOUND METHOD AND DEVICE FOR REPRESENTING THE PROPAGATION OF ULTRASOUND WAVES IN A GUIDE OF LINEARLY VARIABLE THICKNESS

The invention relates, in general, to the representation in a frequency-wavenumber frame, of the propagation of one or more ultrasound waves in a guide, or guided modes, in the case where the thickness of the guide is linearly variable.

The invention relates, in particular, to the representation of one or more modes guided by the cortex or cortical part of a human long bone, insofar as such a bone may be approximated by a guide of linearly variable thickness. The invention is aimed especially at aiding the evaluation of the risk of fracture, in a non-intrusive manner in the human body, of osteoporosis, by estimating the elastic and geometric properties (especially thickness) of the bone, based on the representation of the guided modes, versus wavenumber or versus phase velocity, as a function of temporal frequency.

Hereinafter, "polynomial of degree n of the variable x" will designate a mathematical function $f(x) = C_0 + C_1 \cdot x + \ldots + C_n \cdot x^n$ where $C_0$ is the coefficient of degree 0 in x of the polynomial, where $C_1$ is the coefficient of degree 1 of the polynomial, which may in the patent application be denoted by C with no subscript, and where $C_n$ is the coefficient of degree n of the polynomial.

Hereinafter, "dihedral guide" will designate a guide for ultrasound waves, of linearly variable thickness, especially a guide limited by two wedge-like planes, exhibiting a deficiency of parallelism between the planes, said deficiency being limited to a few degrees of angle.

Hereinafter, norm of a vector with "n" components in a space with "n" dimensions, designates the Euclidean norm or 2 norm of this vector, equal to the square root of the sum of the squares of the components of the vector.

Hereinafter, the word "Pi" or the symbol "π" will designate the ratio of the perimeter of a circle to its diameter.

Hereinafter, "wavenumber" will designate the number of spatial periods or wavelength of a wave over the perimeter of a circle of diameter 1, denoted k with $$k = \frac{2 \cdot \pi}{\lambda}$$

where λ is the wavelength.

Hereinafter, "angular frequency of a wave" will designate the number of temporal periods of a wave over the perimeter of a circle of diameter 1, denoted ω with ω=2.π.f. where f is the temporal frequency, the inverse of the temporal period T, with f=1/T.

Hereinafter, "phase velocity" will designate the ratio of the angular frequency of an ultrasound wave to its wavenumber, denoted $$v_\varphi = \frac{\omega}{k}.$$

A sinusoidal plane wave progressing in the direction of increasing x will be defined on M receivers positioned at discrete values of the spatial variable x, by its complex amplitude proportional to: $W(t,x) = e^{-i(\omega \cdot t - k \cdot x)}$.

Hereinafter, "discrete temporal Fourier Transform for the angular frequency ω" will designate, for a signal V(t) defined on discrete values of the temporal variable t, the scalar product of the vector of the values of V(t) and of the vector of the values of a sinusoidal wave $T(t) = e^{+i \cdot \omega \cdot t}$ over discrete values of the time, with i the complex root of –1 and ω the angular frequency of the wave.

Hereinafter, "discrete spatial Fourier Transform in the spatial direction x for the constant, real wavenumber k" will designate, for a signal V(x) defined on M receivers positioned at discrete values of the spatial variable x, the scalar product of the vector of the values of V(x) and of the vector of the values of a plane wave $$T(x) = \frac{1}{\sqrt{M}} \cdot e^{-ikx}$$

on the receivers, with i the complex root of –1 and k the wavenumber of the plane wave. The vector T(x) is of Euclidean norm equal to 1.

Hereinafter, "modified discrete spatial Fourier Transform, in the spatial direction x for the real wavenumber k(x), varying along x" will designate, for a signal V(x) defined on M receivers positioned at discrete values of the spatial variable x, the scalar product of the vector of the values of V(x) and of the vector of the values of a modified plane wave $$T(x) = \frac{1}{\sqrt{M}} \cdot e^{-ik(x) \cdot x}$$

on the receivers, with i the complex root of –1 and k(x) the wavenumber varying with x. The vector T(x) is of Euclidean norm equal to 1.

Hereinafter, for a rectangular matrix S with M rows and N columns, the matrix possibly being square if M=N, the expression "Singular value decomposition of numerical rank R", with R less than or equal to the minimum of M and of N, will designate a singular value decomposition of the matrix S, numerically reduced to the largest R singular values, either by specifying the number R of singular values to be preserved starting from the highest for singular values arranged in descending order, or by specifying a threshold, chosen in consideration of the noise, below which a singular value is neglected. In particular, the singular value decomposition produces singular output or reception vectors, associated with the singular values, which are mutually orthogonal and each normed to unity and which will be interpreted hereinafter as a basis of the space of the signals received or recorded or output signals. The singular value decomposition also produces singular emission or input vectors, associated with the singular values, which are mutually orthogonal and each normed to unity and which will be interpreted hereinafter as a basis of the space of the signals emitted or input signals.

Hereinafter, a sensor, emitter or receiver with piezoelectric effect or, equivalently, using any other effect able to sense, emit or receive an ultrasound wave and convert it into an electrical and then digital signal, will be referred to respectively as an ultrasound sensor or ultrasound emitter or ultrasound receiver.

The prior art before the invention includes in particular the French patent application published under the N° FR2946753, relating to a device and a method for representing the modes of propagation of an ultrasound wave in a plane and parallel guide, of constant thickness, with the intention of using this representation to measure physical characteristics of a human long bone and especially of its cortical layer.

This prior art uses a singular value decomposition of the temporal Fourier transforms of an ultrasound signal on receivers, originating from emitters, and a projection of a plane wave of constant wave vector into the basis of the singular reception vectors, to improve the determination of the propagation of the ultrasound wave in a plane guide with parallel faces, of constant thickness, such as a plate, and apply it to a bone.

However, the application of this prior method, which is suitable solely for a plane and parallel guide, of constant thickness, to a long bone causes biases or errors for the prior art.

Indeed, a human long bone has a variable cortical thickness which makes it necessary to consider it, for an ultrasound wave received by a linear array or probe of ultrasound sensors, roughly aligned with the most extended direction of the long bone, to be a dihedron of small vertex angle (0° to 3° of angle, commonly with a value of 1° of angle). In such a guide, the ultrasound wave propagating by convention toward the vertex of the dihedron may not, in practice, be likened to a plane wave except over an infinitesimal part of the guide. This results in a systematic error or bias in the determination of the representation of the propagation modes of a long bone with the prior art method, these modes being in particular different from the modes of a plate of constant thickness.

The signal processing of the prior art hereinabove thus turns out to be insufficient to accurately measure the propagation modes of a human bone, regarded as a guide of linearly variable thickness.

The prior art also includes attempts to locally approximate a dihedral guide to a parallel plane guide, by limiting the number of receivers used to represent the guided waves, by sub-windows. However, this strategy is heavily penalizing in regard to signal/noise ratio and resolution, which deteriorate as the number of receivers and therefore of signals decreases. Moreover, bone is an absorbent medium of irregular geometry, thereby limiting the possible number of receivers. Thus, in practice, these attempts are attended by numerous drawbacks, mainly due to necessarily overly significant distances between emitters and receivers and a necessity to ascertain the thickness of the guide under each reception sub-window.

There does not therefore exist in the prior art any device or method for representing the propagation modes of a dihedral guide, which would nevertheless be directly applicable to the ultrasound measurement of the modes guided by a human long bone.

Advantageously, such a method for representing the propagation modes of a dihedral guide ought to be obtained based on piezo-electric ultrasound sensors, extending as a linear array in a direction, over a straight line and according to a regular pitch, to exploit elements which exist in the prior art.

In this context, the invention relates to:

A device for the representation, in a frequency-wavenumber frame f-k, of the propagation of an ultrasound wave in a dihedral guide, which comprises ultrasound emitters referenced by "Ej" with j an integer varying between 1 and N, N a strictly positive integer and ultrasound receivers referenced by "Ri" with i an integer varying between 1 and M, M a strictly positive integer, the receivers being disposed spatially over a first segment of a straight line according to a regular pitch "A", which comprises means for processing the signal received by the receivers, originating from the emitters, in which the processing means comprise means for calculating a modified discrete spatial Fourier transform, for a spatial integration variable "x", centered in the middle of said first segment and traversing the receivers in the direction of increasing x, and for a wave vector k(x) equal to a product k.P(x), with k a coefficient which is constant in x and lies between 0 and 2*Pi/A, and with P(x) a polynomial in x, of coefficient of degree 0 in x equal to 1 and of coefficient "C" of degree 1 in x such that C.A lies between −¹⁄₁₀ and +¹⁄₁₀.

In variants of the device hereinabove:
the emitters are disposed on said straight line.
the emitters are disposed on said straight line according to the pitch "A" and form with the receivers an array extending linearly in the direction of said straight line.
the emitters and the receivers are piezo-electric sensors.
the means for processing the signal comprise converters of an analog signal into a digital signal.
the calculation means are digital.

The invention also relates to a method of using the device hereinabove for the representation, in a frequency-wavenumber frame f-k, of the propagation of an ultrasound wave in a dihedral guide, at a temporal frequency f0 and at a wavenumber k0, comprising the following steps:

emitting in the guide, a time-dependent ultrasound signal with wide passband including the frequency "f0", by an emitter Ej with j a chosen integer between 1 and N;

receiving the signal propagated in the guide, as a function of time, on the receivers Ri with i a chosen integer between 1 and M;

calculating a discrete temporal Fourier transform of the signal received at the frequency f0 and placing the result Sij in the i-th row and the j-th column of a rectangular matrix S(f0) with M rows and N columns;

filling the matrix S(f0), by repeating the previous operations for the receivers other than Ri and for the emitters other than Ej;

decomposing the matrix S(f0) into singular values by fixing a numerical rank "R" of the matrix 5, with R a chosen integer between 1 and N, to obtain a number R of singular reception vectors referenced by "Ur(f0)" with r an integer varying between 1 and R;

calculating a modified discrete spatial Fourier transform of the singular reception vectors Ur (f0), for a spatial integration variable "x" centered in the middle of said first segment and traversing the receivers and for a wave vector k(x) equal to k0, chosen between 0 and 2.Pi/A, multiplied by a polynomial in x "P(x)", of coefficient of degree 0 equal to 1 and of coefficient "C" of degree 1 in x such that C.A is variable between −¹⁄₁₀ and +¹⁄₁₀;

calculating a function "Norm(f0,k0,C)", equal to the sum of the moduli squared of the modified discrete spatial Fourier transforms of the singular reception vectors Ur (f0) over the range of variation of C, determining the value C=Cmax for which Norm(f0,k0,C) is maximum, over the range of variation of C;

representing in the frame f-k, the propagation of the ultrasound wave in the dihedral guide, versus f0 and k0, by referring the value of the maximum Norm(f0,k0, Cmax) to the point (f0,k0) of the frame.

The invention also relates to an application of the method hereinabove to obtain the representation, in the frame f-k, of the propagation of the ultrasound waves in the dihedral guide, by referring the value of the maximum Norm(f,k, Cmax(f,k)) to the point (f,k) of the frame, for k varying between 0 and 2.Pi/A and f varying over the frequencies of the wide passband.

The invention also relates to an application of the method hereinabove in which the dihedral guide is a human long bone.

The invention is described in conjunction with figures numbered 1 to 3:

FIG. 1 which represents a dihedral guide (1) surmounted by a linear array, divided into a set of emitters (2) and a set of receivers (3), of sensors in contact with the guide.

Figure 1:
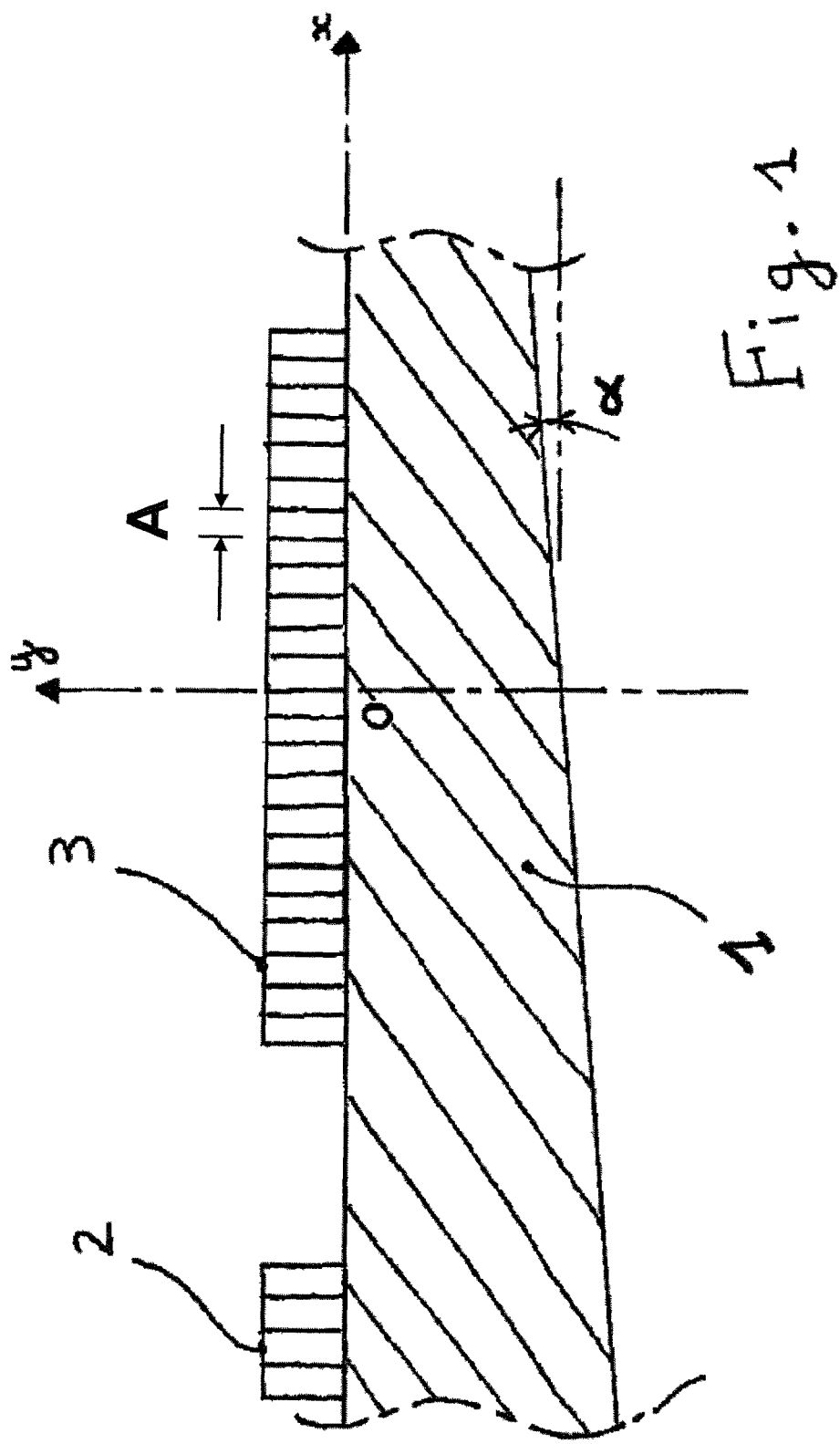

With reference to FIG. 1, in an orthonormal frame Oxyz of a Euclidean space, a dihedral guide (1) is composed of a material such as human bone or a phantom material of such a bone such as glass fibers embedded in a commercially available epoxy material. The dihedral guide extends between a first plane xOz and a second plane passing through the point x=0, y=−e0, z=0, parallel to the axis Oz and making, in projection in the plane xOy, an angle "α" or alpha=+2° of angle with the axis Ox, in the plane xOy oriented for the angles in the direct trigonometric sense. The guide is thus of a thickness e dependent on x, given by the formula: $e(x)=e0.(1-\tan(alpha).x)$, e decreasing toward increasing x. For this example, e0 equals 2.2 mm.

A series of N emitters (2), equal to 5 in number, is regularly disposed according to a pitch "A" of 0.8 mm on the x axis at negative values of x and are separated by a zone which is absorbent in respect of acoustic waves, from a set of M receivers (3), equal to 24 in number, regularly spaced according to the pitch A, between the positions x=−11.5.A and x=11.5.A, in intervals of the pitch A, in a symmetric manner about the origin O of the frame, on the x axis. The pitch A fixes the maximum value of the wavenumber k=2.Pi/A=7.8 mm-1 that the receivers can detect.

The emitters are linked in a known manner to a signal generator across a multiplexer making it possible to select sequentially over time one out of the N emitters.

The receivers are linked in a known manner to an analog-digital converter across a multi-channel electronic demultiplexer, enabling the signal from the receivers to be digitized sequentially over time, in the form of digital data.

The analog-digital converter is supplemented in the processing means by a calculator and calculation means, able to process the data digitally by program according to mathematical methods and by means of on-screen display of the data, as false colors or as gray levels or as level curves or in a three-axis representation.

The processing means are also capable of activating an emitter so as to propagate an ultrasound, wideband signal which includes a given temporal frequency "f0", in the dihedral guide toward the decreasing thicknesses, of digitizing in a vector with M components, the signal received by each receiver as a function of time, originating from the emitter and of calculating the discrete temporal Fourier transform thereof at the frequency f0.

The processing means are also capable in a known manner of successively activating each emitter and digitizing the signals received on the receivers so as to form a set of N vectors of reception signals with M components which bring together into a table with M rows and N columns, the temporal Fourier transforms at f0, of the signals received by the M receivers originating from the N emitters, and of storing them in a table addressable by the calculation means by the name "matrix S(f0)" or "S(f0)".

The processing means may also be capable of calculating the Fourier transform of the signal over a set of frequencies of the wide band of the signal emitted and of storing these values with a view to calculating a set of matrices S(f) referenced by a set of frequencies f chosen in the band of the signal emitted. This strategy makes it possible to proceed in parallel for all the frequencies of interest and to obtain a three-dimensional tensor S(f). This strategy makes it possible to avoid re-emitting for each frequency of interest and to best exploit the wideband emission signal.

The set of material operations culminating in rendering available in a table and a matrix S(f0), the temporal Fourier transforms at f0, of the signals of the receivers that have passed through the dihedral guide after having been emitted by an emitter, is referred to hereinbelow as "firing".

On completion of a firing, the means of calculations have available at f0, a rectangular table or matrix S(f0) of dimensions M×N with M greater than or equal to N, in the mode described.

In a manner known from the prior art, it is possible to calculate the singular value decomposition of the matrix S(f0), reduced to a numerical rank R of less than or equal to N. This operation is known in numerous mathematical libraries and the empirical choice of the rank R can be made as a function of the noise conditions encountered by the person skilled in the art, by simple routine trials.

In this operation R singular values are calculated and R singular reception vectors with M components are calculated, these vectors are mutually orthogonal and normed to 1.

A series of test vectors corresponding to modified plane waves whose wavenumber is a vector k(x) equal to a coefficient k0 which is constant in x and which is multiplied by a polynomial of degree 1 in x, whose coefficient of degree 0 in x equals 1 and whose coefficient C of degree 1 in x can vary in such a way that the product C.A, of C and of the pitch A between the receivers, varies between −0.1 and +0.1, with x centered in the middle of the segment of the receivers, is then projected onto the singular reception vectors.

This operation is equivalent to forming the modified discrete spatial Fourier transform of the singular reception vectors.

In a general manner, the variation of C proposed for the invention is aimed at best describing best the fluctuations versus x of the wavenumber, in a zone of variation, called the range of "adiabatic variation of the modes", of the modes of a dihedral guide for dihedral angles corresponding to the linear variation of thickness of a long bone. In this approximation the waves propagating in the direction x are plane waves in the direction x, whose wavenumber is continuously variable versus x. Any polynomial or functional approximation making it possible to account for a continuous variation of the wavenumber or of the wavenumber of the modes of a dihedral guide or of a long bone, according to an expected law, would thus be in accordance with the teaching of the invention.

It would remain within the teaching of the invention to increase the degree of the polynomial beyond 1 so as to improve the method through the use of a vector $k(x)=k0.(1+C.x+\ldots+C_n.x^n)$ where k and $C, \ldots, C_n$ are constant in x, non-zero and unknown a priori, but to the detriment of the calculation time, as explained hereinbelow. For an assumed limited calculation power and practical operation of real-time presentation of the propagation modes on the screen in the adiabatic approximation, the terms of degree greater than 1 in P(x) will therefore not be considered in the disclosure hereinbelow. For dihedral guides of small angle which is representative of the variation of the cortical thickness of a long bone, the Applicant has thus calculated that the modes of such a guide have a wavenumber which varies as a function of x with a wavenumber k(x) which may be usefully approximated by $k(x)=k0.(1+C.x+ \ldots +C_n.x^n)$ where k and C, . . . , $C_n$ are constant in x and unknown a priori and where k0 is the wavenumber at x=0.

The coefficients of the polynomial are nonetheless dependent on the temporal frequency and on the guided mode considered, thus not allowing a priori approximation, by a polynomial dependent solely on the angle of the dihedron, in a frame f-k.

This approximation can be referred to a polynomial $k(x)=k0.(1+C.x)$ for most practical cases with k0 lying between 0 and 2.Pi/A where A is the pitch of the receivers and C can vary in such a way that C.A remains between −0.1 and +0.1 over the whole of the range of adiabatic variation of the propagation modes and predominantly between −0.05 and +0.05 in the majority of cases encountered in respect of human bone.

In the particular case of propagation toward decreasing thicknesses, the values of C are predominantly negative, thereby making it possible to restrict the domain of searches for the values of C and to decrease the calculation time with the invention. Moreover, the method according to the invention is particularly effective in this direction of propagation.

The method of the invention for calculating the propagation modes of a dihedral guide then consists essentially:

in choosing in the plane (f,k), a point (f0,k0) where one wishes to represent the propagation modes, with f0 in the frequency passband of a wideband emission signal and k0 constant in x and chosen between 0 and 2.Pi/A where A is the spacing between receivers regularly distributed in a direction x in calculating the matrix S(f0)

in decomposing it into singular values of given numerical rank in calculating a modified discrete spatial Fourier transform, of the singular reception vectors for a spatial integration variable "x" centered in the middle of said first segment and traversing the receivers and for a wavenumber varying with x k(x) equal to the coefficient k0, constant in x and chosen between 0 and 2.Pi/A, multiplied by a polynomial P(x) of coefficient of degree 0 equal to 1 and of coefficient "C" of degree 1 in x, varying in such a way that C.A lies between −1/10 and +1/10 in determining the value C=Cmax for which a function "Norm(f0,k0,C)", lying between 0 and 1, equal to the sum of the moduli squared of the modified discrete spatial Fourier transforms of the singular reception vectors attains a maximum of value Norm(f0,k0,Cmax) over the range of variation of C. If appropriate, the polynomial P(x) will advantageously be able to be chosen of degree greater than 1, if Cmax.A attains its minimum (−10%) or its maximum (+10%) for k0,f0, to the detriment of the calculation time in representing the propagation modes of the guide of variable thickness, in a two-dimensional frame f-k, at the point (f0,k0) by graphically referring the value of the maximum Norm(f0,k0,Cmax) to the point (f0,k0) in f-k by an indication of gray level or of a color scale, if appropriate a representation with three axes or based on level lines can be used.

The method having been detailed for obtaining a representation at a point (k0,f0) of the frame f-k, it is then easy to repeat it via the operation consisting in:

making (f0, k0) vary so as to traverse the plane f-k and representing therein the signal at any desired point (f,k), by referring the value of the maximum Norm(f, k,Cmax(f,k)), in the limits of variations fixed by A for k and by the passband of the emission signal for f.

It should be noted that the method makes it possible to determine the presence of the guided modes in the frame k-f without any a priori presumption about the thickness and the material. In particular it will be possible to determine, without any a priori presumption, the presence of several modes at one and the same temporal frequency.

The representation of the modes may, for example, be done by associating a gray level or a color intensity with ranges of values between 0 and 1 of the value of Norm(f, k,Cmax(f,k)) and by presenting it on the screen to an operator, if appropriate a representation with three axes or based on level lines can be used.

The representation of the modes is independent of the operator, except for the choice of a numerical rank R fixed as a function of the signal-to-noise ratio encountered in practice and the choice of a threshold for Norm(f,k,Cmax (f,k)), above which the values of this Norm are preserved.

Equivalently, the processing means will be able to be supplemented with a means for an operator to choose a representation threshold corresponding to a value of Norm (f,k,Cmax(f,k)) below which, the modes are not represented in the plane f-k.

The method or process of the invention requires only that the wave vector or constant wavenumber k0 of the test vectors be replaced in the calculations of k0, which are known from the prior art, by application of the singular value decomposition, by a wave vector varying with x, approximated by a polynomial of degree 1 multiplying k0 for small values of x, thus corresponding to a finite expansion of k(x) of order 1 in x about the value of k0 at x=0, in the middle of the segment of the receivers. Thereafter, a search is conducted for an absolute maximum of a function of a variable C or of several variables C, C2, . . . , Cn instead of a single variable if a polynomial of degree greater than 1 is used, corresponding to a finite expansion of order n of k(x) about k0. The chosen norm remaining the same, the generalization to several coefficients C, C2, . . . , Cn is therefore particularly easy. The method of the invention is thus adaptable to the search for polynomial coefficients of degrees greater than 1, if the calculation power allows the search for a maximum of a function of more than one variable.

The use of the method of the invention therefore requires only an ultrasound device comprising a calculation means making it possible to replace in the spatial Fourier transform in x for a wave vector k0, the wave vector k0 by a wave vector k(x) with $k(x)=k0.(1+C.x)$ where C can vary in such a way that the product C.A, of C and the pitch A between the receivers, varies between −10% and +10%.

By way of particular case, it may be noted that the spatia-temporal Fourier transform can be regained by fixing N (number of emitters) at 1 and C at 0.

In the case of FIG. 1, the calculation will finally be able to be performed in the manner hereinbelow, described by comparison with the prior art.

A wide passband signal containing a frequency f0 is applied to each emitter or transmitter and the corresponding signal $s(t, x_i^R, x_j^E)$ is recorded as a function of time on each receiver and the temporal Fourier transform thereof at the frequency f0 of the reception signals is performed to obtain a signal $Sij=S(f0,x_i^R,x_j^E)$.

After this operation, there is obtained a matrix S(f0) of N rows, each row corresponding to a given transmitter and of M columns, each column corresponding to a given receiver, whose values S(f0,i,j) are equal to the Fourier transform at the frequency f0 of the signal emitted between the emitter j and the receiver i.

Thereafter, there is undertaken a singular value decomposition of the matrix S(f0) and, for example, a thresholding so as to preserve only a number of singular values which is smaller than the total number of these values by eliminating the lowest singular values that are smaller than a threshold determined experimentally as a function of the noise. The rank of the matrix of singular values is then numerically fixed.

The singular value decomposition makes it possible to obtain at the same time as the singular values a basis of singular reception vectors and the deletion of certain singular values thus makes it possible to obtain a set of orthogonal singular reception vectors that are associated with the singular values preserved in number equal to the rank, denoted by "R", of the matrix of the singular reception vectors.

In the prior art, a test vector of wavenumber k0 is selected in the basis of the singular reception vectors whose norm is equal to 1. This test vector is of form on the receivers:

$$e_{test} = \frac{1}{\sqrt{M}} \exp(-i \cdot k0 \cdot x)$$

This form corresponds to a progressive plane wave on the receivers, in the direction of positive values of x and of constant wave vector k0.

The projection of this test vector in the sub-space of the signal, that is to say over the singular reception vectors, then makes it possible to obtain a function which is a norm dependent on f0 and on k0, which is expressed by:

$$Norm(f0, k0) = \sum_{n=1}^{R} |\langle e_{test}(k0) | U_n(f0) \rangle|^2$$

This summation operation is performed on the singular reception vectors and makes it possible to obtain a Norm (f0,k0) for the direction of propagation over the reception zone (toward increasing x).

It corresponds to a summation of the moduli squared of the Fourier transforms at k0, of the singular reception vectors. It also corresponds to the Euclidean norm of the test vector in the basis of the singular reception vectors.

The Fourier transform may be interpreted here as a scalar product (denoted "I") of the test vector and of each singular vector. In practice, projection of the test vector over the basis of the singular reception vectors is thus equivalent to performing the discrete spatial Fourier transform of the singular vectors.

This norm therefore corresponds also to the sum of the squares of the norms of the Fourier transforms of the singular reception vectors.

To implement the invention, it suffices in the method of the prior art, to modify the test vector chosen in the calculation of the Norm by the new formula:

$$e_{test} = \frac{1}{\sqrt{M}} \exp(-i \cdot k(x) \cdot x)$$

With $k(x)=k0 \cdot (1+C \cdot x)$ k0 chosen over between 0 and $2 \cdot Pi/A$ with A pitch of the receivers and with C variable so that A.C varies over [−10%;+10%].

A norm dependent on f0,k0 and C is then obtained, f0 and k0 being fixed:

$$Norm(f0, k0, C) = \sum_{n=1}^{R} |\langle e_{test}(k0, C) | U_n(f0) \rangle|^2$$

For which the maximum for C=Cmax is sought over the domain of C, for f0 and k0 fixed.

In order to represent the propagation modes of a guide of slowly varying thickness, independently of the angle of the dihedron of the guide, it then suffices to chart on a graph in two dimensions, the value of the maximum found of the norm Norm(f0,k0,Cmax) which is between 0 and 1, for the point (f0,k0) chosen in the plane f-k.

Finally, it will suffice to choose other points (f1,k1), . . . (fn,kn) in the plane f-k to plot a representation of the propagation modes of the guide of slowly varying thickness, independently of the variation of thickness of the guide.

This results in a robust representation of the propagation modes of a guide of slowly varying thickness.

The invention has been tested for dihedral angles of 1° and 2° which are representative of the dihedral angles of a long cortical bone such as the human radius.

Figure 2:
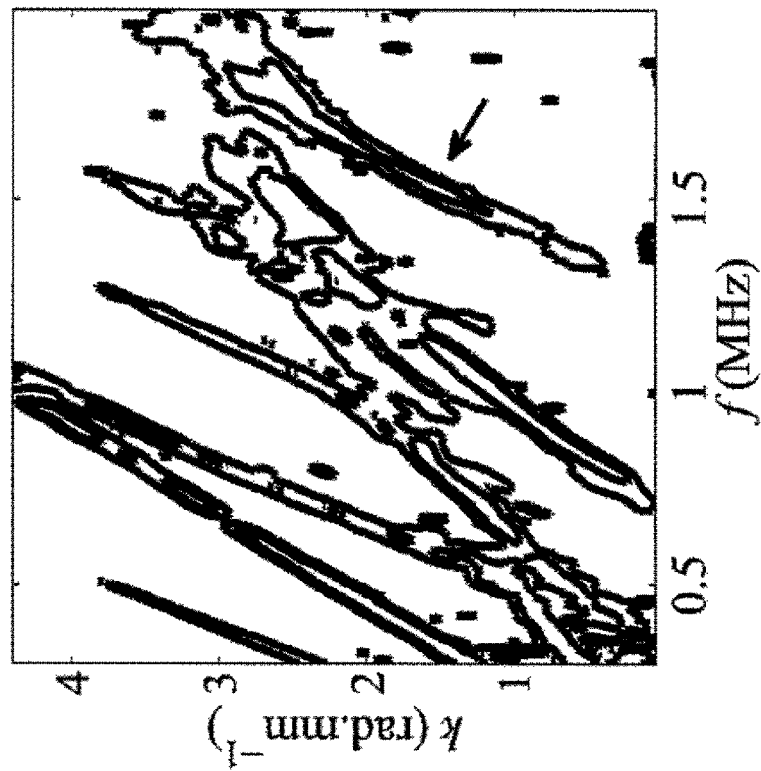
FIG. 2 shows the representation of the propagation modes of a guide with a dihedral angle of 2° for the prior art, especially patent application FR2946753 and for a thickness equal to 2.2 mm in the middle of the receivers. The material of the guide is a commercial bone phantom, composed of glass fibers in an epoxy.
Figure 3:
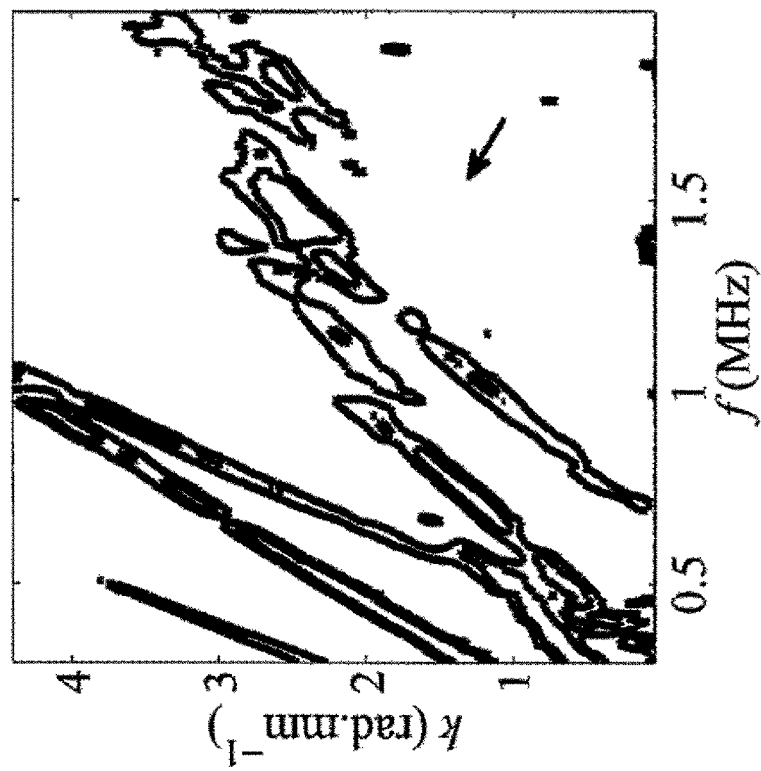
FIG. 3 shows the representation of the propagation modes of the same guide as FIG. 2 with the invention.

In FIGS. 2 and 3, the representation chosen for the guided propagation, is as level lines with a threshold greater than 0.5, for the values adopted for Norm(f,k,C=0) and Norm(f,k,C=Cmax). At each point, if Norm(f,k,C=0)<0.5, in FIG. 2, or Norm(f,k,C=Cmax)<0.5,in FIG. 3, the level curve of Norm(f,k,C=Cmax) is thus not represented. The 0.5 and 0.7 level curves are thus represented in these figures.

In FIG. 2, the representation of the propagation modes of a guide with a dihedral angle of 2° in the prior art is presented by the values of Norm(f,k,C=0). An absence of propagation mode is noted in a zone defined by f>1.5 Mhz and k<2 rad.mm-1.

In FIG. 3, the representation of the propagation modes of the same guide with a dihedral angle of 2° and with application of the invention is presented by comparison, by the values of Norm(f,k,C=Cmax).

It is observed that the structure of the whole set of modes is preserved globally, between the two figures for low values of f and k.

However, at least one mode, whose position is indicated by an arrow in FIGS. 2 and 3, and that can be retrieved by finite element simulation, as being present in the zone f>1.5 MHz and k<2rad.mm-1, is sharply revealed in FIG. 3 by the invention whereas it is not observable in FIG. 2. It is possible to compare the modes obtained with the theoretical modes of a plate of constant thickness equal to e0, thickness at the level of the middle of the segment of the receivers.

It is thus possible to verify that for a given ultrasound probe, with respect to a numerically calculatable or simulatable theoretical case, the propagation modes of a dihedral guide are effectively represented in larger number with the invention than with the prior art. The invention therefore presents an advantage in the representation of the propagation modes of a guide of slowly varying thickness, within the sense of the adiabatic approximation and therefore for the study of the cortical part of a real human bone.

The invention is therefore susceptible of industrial application or useful as an aid to the evaluation of a risk of fracture of osteoporosis or of other bone diseases.

Within the meaning of the patent application, the following sensors in particular will be considered to be equivalents of the piezo-electric ultrasound sensors described:

CMUT ("Capacitive micromachined ultrasonic transducers") sensors;

sensors using lasers both to emit an ultrasound wave and to detect it.

Within the meaning of the patent application, the representation in a frequency-phase velocity frame of the propagation of the ultrasound waves in a guide will be considered to be an equivalent to a representation in a frame f-k of the propagation of these waves.

Within the meaning of the present patent application, it will be considered equivalent to use a greater number of emitters N than the number M of the receivers for the implementation of the invention, the numerical rank R being chosen smaller, in this case smaller than or equal to M. The rank R will thus be chosen, in all the cases of the invention, smaller than or equal to the lower of the number N of emitters and of the number M of receivers.

Within the meaning of the present patent application, it will be considered equivalent to exchange the role of the emitters and of the receivers, for the implementation of the invention, the use of the singular reception vectors then being replaced with the use of the singular emission vectors in the disclosure hereinabove.

Within the meaning of the present patent application, it will be considered equivalent for the implementation of the invention, that the array be in contact with the guide or be separated from the latter by soft tissues, while being parallel to the surface of the guide which is closest to this array.

Within the meaning of the present patent application, "digital means of calculation" will in particular be able to consist of a computer executing a program or to comprise such a computer.

The invention claimed is:

1. A device for the representation, in a frequency-wavenumber frame, of the propagation of an ultrasound wave in a dihedral guide, the device comprising:

ultrasound emitters referenced by Ej with j an integer varying between 1 and N, N a strictly positive integer;

ultrasound receivers referenced by Ri with i an integer varying between 1 and M, M a strictly positive integer; and means for processing and outputting the signal received by the receivers, originating from the emitters, wherein the receivers are disposed spatially over a first segment of a straight line according to a regular pitch A that is a scalar length value, the processing means comprise means for calculating a modified discrete spatial Fourier transform, for a spatial integration variable x, centered in the middle of said first segment and traversing the receivers in the direction of increasing x, and for a spatially-varying wave vector k(x) equal to a product k.P(x), k is a wavenumber coefficient which is constant in x and lies between wave vector values 0 and 2*Pi/A, 2*Pi/A is a wave vector value defined by diving 2*Pi by the regular pitch A, P(x) is a polynomial in x, of coefficient of degree 0 in x equal to 1 and of coefficient C of degree 1 in x such that C.A lies between −1/10 and +1/10, and C.A is a scalar value defined by multiplying the coefficient C of degree 1 in x by the regular pitch A.

2. The device as claimed in claim 1, in which the emitters and the receivers are piezo-electric sensors.

3. The device as claimed in claim 1, in which the means for processing the signal comprise converters of an analog signal into digital signal.

4. The device as claimed in claim 1, in which the calculation means are digital.

5. The device as claimed in claim 1, in which the emitters are disposed on said straight line.

6. The device as claimed in claim 5, in which the emitters are disposed on said straight line according to the regular pitch A and form with the receivers an array extending linearly in the direction of said straight line.

7. A method of using the device as claimed in claim 1 for the representation, in the frequency-wavenumber frame, of the propagation of the ultrasound wave in the dihedral guide, at a temporal frequency f0 and at a wavenumber k0, the method comprising:

emitting in the guide, a time-dependent ultrasound signal with wide passband including the frequency f0, by the emitter Ej with j the chosen integer between 1 and N;

receiving the signal propagated in the guide, as a function of time, on the receivers Ri with i the chosen integer between 1 and M;

calculating a discrete temporal Fourier transform of the signal received at the frequency f0 and placing the result Sij in the i-th row and the j-th column of a rectangular matrix S(f0) with M rows and N columns;

filling the matrix S(f0), by repeating the previous operations for the receivers other than Ri and for the emitters other than Ej;

decomposing the matrix S(f0) into singular values by fixing a numerical rank R of the matrix S, with R a chosen integer between 1 and N, to obtain a number R of singular reception vectors referenced by Ur (f0) with r an integer varying between 1 and R;

calculating a modified discrete spatial Fourier transform of the singular reception vectors Ur (f0), for the spatial integration variable x centered in the middle of said first segment and traversing the receivers and for the wave vector k(x) equal to k0, chosen between 0 and 2*Pi/A, multiplied by the polynomial in x P(x), of the coefficient of degree 0 equal to 1 and of the coefficient C of degree 1 in x such that C.A lies between −1/10 and +1/10;

calculating a function Norm(f0,k0,C), equal to the sum of the moduli squared of the modified discrete spatial Fourier transforms of the singular reception vectors Ur (f0) over the range of variation of C;

determining the value C=Cmax for which Norm(f0,k0,C) is maximum, over the range of variation of C;

representing in the frame, the propagation of the ultrasound wave in the dihedral guide, versus f0 and k0, by referring the value of the maximum Norm(f0,k0,Cmax) to the point (f0,k0) of the frame.

8. The method as claimed in claim 7, further comprising referring the value of the maximum Norm(fp,kp,Cmax (fp,kp)) to the point (fp,kp) of the frame, for values of wide passband wavenumber coefficient kp between 0 and 2*Pi/A and values of wide passband frequency fp over the frequencies of the wide passband.

9. The method as claimed in claim 8, wherein the dihedral guide is a human long bone.

\* \* \* \* \*